US008425395B2

(12) United States Patent
Kraus et al.

(10) Patent No.: US 8,425,395 B2
(45) Date of Patent: Apr. 23, 2013

(54) IMPLANTABLE DEVICE, SYSTEM FOR GENERATING LOCALISED ELECTROMAGNETIC FIELDS IN THE AREA OF AN IMPLANT AND COIL ARRANGEMENT

(75) Inventors: Werner Kraus, München (DE); Stephanie Kraus, Bad Tölz (DE); Heribert Stephan, München (DE)

(73) Assignee: Neue Magnetodyn GmbH, Munich (DE)

( * ) Notice: Subject to any disclaimer, the term of this patent is extended or adjusted under 35 U.S.C. 154(b) by 996 days.

(21) Appl. No.: 12/126,455

(22) Filed: May 23, 2008

(65) Prior Publication Data

US 2009/0099404 A1    Apr. 16, 2009

(30) Foreign Application Priority Data

Oct. 16, 2007 (DE) .......................... 10 2007 049 542

(51) Int. Cl.
*A61N 2/08* (2006.01)
(52) U.S. Cl.
USPC ............................................... 600/13; 600/9
(58) Field of Classification Search .................... 600/12, 600/13; 606/60, 300, 301, 280, 286, 289
See application file for complete search history.

(56) References Cited

U.S. PATENT DOCUMENTS

| 3,745,995 A | 7/1973 | Kraus |
| 4,195,367 A | 4/1980 | Kraus |

(Continued)

FOREIGN PATENT DOCUMENTS

| DE | 1918299 | 10/1970 |
| DE | 2611744 A1 | 9/1977 |

(Continued)

OTHER PUBLICATIONS

Yunokuchi K et al: "Developing a More Focal Magnetic Stimlilator. Opart II: Fabricating Coils and Measuring Induced Current Distributions" Journal of Clinical Neurophysiology, Rave~ Press, New York, NY, US, Bd. 8, Nr. 1, 1. Jan 1991.*

(Continued)

*Primary Examiner* — John Lacyk
*Assistant Examiner* — Joshua D Lannu
(74) *Attorney, Agent, or Firm* — The Dobrusin Law Firm P.C.

(57) ABSTRACT

The invention relates to an implantable device to be fixed to a bone and comprising an electrically conductive base body provided with at least two through holes and at least one pair of shaft-shaped contact means, wherein each contact means passes through a through hole of the base body and penetrates a section of the bone in an implanted state, wherein the surface of each contact means comprises a first and a second electrically conductive surface section as well as an electrically insulating surface section separating the electrically conductive surface sections from each other, wherein the first electrically conductive surface section electrically contacts the base body while the second electrically conductive surface section is electrically insulated with respect to the base body, wherein each contact means contains a coil arrangement in its interior by means of which the electrically conductive surface sections of each contact means are electrically coupled, and wherein the coil arrangements of a pair are wound in opposite directions.

15 Claims, 5 Drawing Sheets

U.S. PATENT DOCUMENTS

| | | | | |
|---|---|---|---|---|
| 4,429,690 | A | * | 2/1984 | Angelino-Pievani ......... 606/280 |
| 4,501,265 | A | * | 2/1985 | Pescatore ........................ 600/14 |
| 2003/0050527 | A1 | | 3/2003 | Fox et al. |

FOREIGN PATENT DOCUMENTS

| | | |
|---|---|---|
| DE | 2636818 A1 | 2/1978 |
| DE | 3343182 A1 | 7/1984 |
| DE | 19928449 C1 | 3/2001 |

OTHER PUBLICATIONS

Co-pending U.S. Appl. No. 12/298,398, filed Oct. 24, 2008.

European Office Action, Application No. 08007857.9, Dated Jul. 18, 2008.

German Office Action, Application No. 102007049542.2, Dated Jul. 15, 2008.

International Search Report dated Feb. 16, 2009 (PCT/EP2008/008724).

EP Search Report Dated Feb. 16, 2009 (EP08007857).

Yunokichi K et al.: "Developing a More Focal Magnetic Stimulator. Part II: Fabricating Coils and Measuring Induced Current Distributions" Journal of Clinical Neurophysiology, Raven Press, New York, NY, US XP000574197.

* cited by examiner

IMPLANTABLE DEVICE, SYSTEM FOR GENERATING LOCALISED ELECTROMAGNETIC FIELDS IN THE AREA OF AN IMPLANT AND COIL ARRANGEMENT

CLAIM OF BENEFIT OF EARLIER FILING DATE

The present application claims the benefit of the filing date of German Application No. DE 102007049542.2 (filed Oct. 16, 2007) the contents of which are hereby incorporated by reference in their entirety.

TECHNICAL FIELD

The invention relates to an implantable device to be fixed to a bone, a system for generating localised electromagnetic fields in the area of an implant as well as a coil arrangement which can be advantageously utilised in this connection.

BACKGROUND OF THE INVENTION

In case of a complexly fractured or pathologically destructed bone the restoration or preservation of the original functional shape is an indispensable prerequisite for its physiological regeneration. In this connection metal implants bridging the defect by a screw fixation of the non-injured bone sections or bone stumps to withstand the strain caused by muscle and tendon tension including necessary physiotherapeutic exercises have been used for more than six decades and are still increasingly used. This measure of bone surgery is referred to as "exercise-stable osteosynthesis".

The shape preservation of the defect tubular bone against the physiological axial pressure is achieved by the implantation of a metal tube securing the bone fragments against a twist (torsion) by means of transverse screw fixations at its distal and proximal ends into the marrow cavity of the long bone between the joints. The main area of application of the intermedullary nail also referred to as Küntscher nail after its inventor, the surgeon Gerhard Küntscher, are the lesions in the central third of the long bones (Tibia, Femur and Humerus).

For the stabilisation of juxta-articular, particularly multi-fragmental lesions the intermedullary nail is unsuitable. In these cases the reconstruction of the shape is attempted by a screw fixation of the bone and its fragments by means of support plates of corrosion resistant steel or alloys such as Co, Cr, Mo and titanium alloys attached to their outer surface. The bone anchoring implants may be provided with bio-compatible coatings such as titanium niobium oxinitrite which have a high electric conductivity. In contrast to the intermedullary nail strained by axial pressures the support plate screwed transversely to the long bone axis is mainly stressed by flexion. Its supporting effect therefore depends on and is limited by its fatigue strength. The problem of the support plate osteosynthesis is therefore as follows: In case of given material- and shape-related properties the support plate and its screw fixation on the bone are required to win the race between bone healing and the breakage of the implant with the timely load-stable consolidation of the bone before the elasticity of the support metal comes to an end.

Another complication of bone healing connected to the implantation of foreign body implants of a larger volume is bacterial infection. It develops with the permanent displacement of blood vessels in the bone skin (periosteum) and in the usually thin soft tissue jacket around the implant. With the increasing resistance of certain germs (staphylococcus aureus) to antibiotics a central medicinal problem arises which can frequently only be "solved" by amputation, for example, in the area of the lower limbs. Statistical figures indicate an amputation rate of up to 10% in the area of the distal tibia and the foot. It has been shown for more than three decades in abiological situations in the orthopaedic and trauma surgical clinic that this disastrous trend can be avoided by using the method by Magnetodyn. In recent times, particularly in the past three to four years, the bactericidal effect and the activation of the antibiosis in case of resistant germs achieved by the application of the electromagnetic fields of the method by Magnetodyn could be successfully proved in vitro in fundamental experiments whereby the achievements in case of chronically infected bone defects documented in the clinic could be explained.

The utilisation of implanted bone support plates and bone screws as alternating current electrodes using their contact to the outputs of a secondary coil, the so-called carriers, was already described in the DT 1 918 299.

According to the DT 26 11 744 A1 the technology of the magneto-dynamically induced electro-osteostimulation of the method by Magnetodyn was integrated into the shaft and socket of hip prostheses.

The electro-intermedullary nail including a secondary coil and electrodes in the hollow cylinder of an intermedullary nail was described in the DE 26 36 818.

The DE 199 28 449 C1 relates to the integration of the secondary coil into the axial bore of a bone screw electrically contacting the shaft of the screw and a tip insulated with respect to the shaft. This system is, in practice, referred to as bipolar induction screw system (BISS). The bipolar induction screw as a solitary implant was limited to screw lengths of 75 to 110 mm. In the surgical clinic it is used for the magnetically induced electro-osteostimulation, for example in case of an osteonecrosis of the femoral head or in case of fractures of the femoral neck.

SUMMARY OF THE INVENTION

The invention is based on the object to accelerate the consolidation of a broken bone provided with a supporting implant and to avoid bacterial problems in osteosynthesis and endoprosthetics.

Said object is solved by the features of the independent claims.

Advantageous embodiments of the invention are disclosed in the dependent claims.

The invention relates to an implantable device to be fixed to a bone and comprising an electrically conductive base body provided with at least two through holes and at least one pair of shaft-shaped contact means, wherein each contact means passes through a through hole and penetrates a section of the bone in an implanted state, wherein the surface of each contact means comprises a first and a second electrically conductive surface section as well as an electrically insulating surface section separating the electrically conductive surface sections from each other, wherein the first electrically conductive surface section of each contact means electrically contacts the base body in an implanted state while the second electrically conductive surface section of each contact means is electrically insulated with respect to the base body by means of the electrically insulating surface section in an implanted state, wherein each contact means contains a coil arrangement in its interior by means of which the electrically conductive surface sections of each contact means are electrically coupled, and wherein the coil arrangements of the contact means of one pair are wound in opposite directions. If such a device is fixed to a bone in the intended manner and an external electromagnetic alternating field is applied which has, for example, a magnetising force of 1 to 5 mT and a sinusoidal characteristic with a frequency of 1 to 20 Hz, an electric voltage is induced in the coil arrangements extending along the shaft-shaped contact means, wherein to this end the magnetic field needs to have a component in the direction of the extension of the shaft of the contact means. Since the two poles of a respective coil arrangement are connected to sections of the contact means which are electrically insulated with respect to each other an electric field is generated between the allocated conductive surface sections. Since furthermore one of the surface sections is connected to the electrically conductive base body in an electrically conducting manner and the coil arrangements are further wound in opposite directions voltages having different polarities are generated in the pair of shaft-shaped contact means, wherein the first surface sections of the respective contact means are on an identical potential. Therefore the voltage between the respective second surface sections of the contact means has twice the amount of the voltage generated in each individual contact means. Since the voltage in each individual contact means is limited particularly by the inductivity of the coil arrangement and therefore the extension of the coil arrangement in the direction of the magnetic field is also limited it is, based on the present invention, also possible to generate a voltage which has proved to be particularly effective from a physiological point of view with contact means of a relatively short design.

The invention is further developed in a particularly useful manner in that at least one contact means of a pair is a fixation screw contacting the base body with a screw head and is screwed into the bone with a screw shaft in an implanted state. Even if it is on principle feasible that any fixation means or even other shaft-shaped means which do not or scarcely contribute to the fixation of the bone support plate are provided with the features according to the invention it is still particularly advantageous to integrate the electromagnetic properties of the contact means into a fixation screw of the base body.

In this connection it is particularly useful that both contact means of a pair are fixation screws.

The invention is further developed in a particularly advantageous manner in that the electrically insulating surface section of the fixation screw electrically insulates the screw head with respect to the main part of the screw shaft. Said main portion of the screw shaft is, in the implanted state, the portion which is disposed inside of the bone. Therefore the electric field is advantageously generated over the entire cross section of the bone, adjacent screw shafts as well as the screw shafts and the base body forming counter electrodes.

It is particularly advantageous that a plurality of pairs of shaft-shaped contact means are provided, wherein respectively adjacent contact means have coil arrangements wound in opposite directions. If the so provided contact means are, for example, disposed in a row, an electrical field can be made available over the entire extension of said row of contact means.

It may be contemplated that the base body is an osteosynthesis means.

In this connection it is particularly advantageous that the osteosynthesis means is an implantable bone support plate. Such a bone support plate is fixed on the bone by means of screws which extend mainly perpendicular to the longitudinal axis of the bone. Consequently the screws have a strongly limited length so that only a limited induced voltage can be created. On the basis of the present invention said voltage can be doubled between adjacent complementary screws. Further there is a voltage between the screw shafts and the bone support plate whereby pressure necroses of the bone area under the support plate are avoided.

It may be also contemplated that the base body is an endoprosthesis.

In this connection it is particularly advantageous that the base body is the socket of a joint replacement. Particularly the anchoring of the socket of a hip joint replacement can thus be fashioned so that the vitality and stability of the pelvic bone are preserved by applying the induction of magnetic fields to the implant in optional time intervals.

The invention further relates to a system for generating localised electromagnetic fields in the area of an implant comprising an implantable device to be fixed to a bone comprising an electrically conductive base body provided with at least two through holes and at least one pair of shaft shaped contact means, wherein each contact means passes through a through hole of the base body and penetrates a section of the bone in an implanted state, wherein the surface of each contact means comprises a first and a second electrically conductive surface section as well as an electrically insulating surface section separating the electrically conductive surface sections from each other, wherein the first electrically conductive surface section of each contact means electrically contacts the base body in an implanted state while the second electrically conductive surface section of each contact means is electrically insulated with respect to the base body by means of the electrically insulating surface section in an implanted state, wherein each contact means comprises a secondary coil arrangement in its interior by means of which the electrically conductive surface sections of each contact means are electrically coupled, and wherein the secondary coil arrangements of the contact means of a pair are wound in opposite directions, and comprising a primary coil arrangement generating an electromagnetic field in the area of the contact means as well as an oscillation generator for generating an alternating current in the primary coil arrangement. The cortical fixation by means of a screw fixation of the damaged bone using a support plate determines the direction of the screws substantially perpendicular to the long bone axis. Inevitably it also has to follow the direction of the external induced electromagnetic field. Instead of the solenoid coils required, for example, for the induction of the electro-nail or the long bipolar screws which solenoid coils encase the damaged section of the bone and thus determine the direction of the induced electromagnetic field parallel to the long body and bone axis two magnetic coils arranged in a Helmholtz arrangement on both sides of the damaged bone are required for the induction of the support plate screws.

In this connection it is particularly useful that the primary coil arrangement includes a coil winding having a point of intersection and defining two surfaces by means of an eight-shaped form, said surfaces being oriented with respect to each other at least during the application of the primary coil arrangement so that the magnetic fields generated by a current flow in the primary coil arrangement and passing through the surfaces are substantially unidirectional. Thus a magnetic field having a suitable orientation with respect to screws arranged perpendicular to the bone axis can be generated using a single coil. The effect of two separate induction coils having magnetic fields of the same direction in which the damaged body region rests may also be realised with a single coil in this way.

It is conveniently contemplated that the primary coil arrangement is elastically deformable so that the surfaces can be arranged on opposing sides of the implantable device. Due to the elastic winding the deformation in the sense of the figure eight or of the sign for infinity is enabled. The "loops" generated in the coil by this deformation of the coil winding may be fitted to both sides of a limb.

It may, for example, be contemplated that fixation means cooperating at two positions of the primary coil arrangement opposed to the intersection point are provided by means of which fixation means the orientation of the surfaces with respect to each other can be established and maintained. The fixation means may, for example, be realised by means of belts, snap fasteners, Velcro type fasteners, buckles or the like.

In a particularly advantageous manner it may be contemplated that the intersection point of the primary coil arrangement is fixable by means of a coupling arrangement. Such a coupling arrangement may, for example, be realised by an elastic belt including a Velcro type fastener or a belt buckle.

It is particularly advantageous that the position of the intersection point and therefore the dimensions of the surfaces are variable. With the surface ratio of the coil loops selectable in this manner the magnetic induction flux density defined as the quotient of the magnetic flux and the considered surface is adjustable. The ratio of the induction flux densities is the reciprocal value of the ratio of the respectively associated surfaces. The surface ratio of the two loops may be selected in accordance with the therapeutic requirements by enabling a variable fixation of the intersection point by a variable arrangement of the coupling arrangement. For example a high magnetic induction flux density may be achieved in a target area of the body by arranging a coil loop having a small surface area in its vicinity while with respect to the other coil surface having a large surface area for providing the Helmholtz coil effect mainly its parallel arrangement relative to the smaller surface is to be taken into account.

The invention further relates to a coil arrangement, particularly for the utilisation in a system according to the invention for generating localised electromagnetic fields in the area of an implant, comprising a coil winding including an intersection point and defining two surfaces by means of an eight-shaped form, the surfaces being oriented with respect to each other so that the magnetic fields generated by a current flow in the coil arrangement and passing through the surfaces are substantially unidirectional. In this way the advantages and particularities of the system according to the invention are also realised within the framework of a coil arrangement. This also applies to the particularly preferred embodiments of the coil arrangement according to the invention described below.

It is further developed in a useful manner in that the coil arrangement is elastically deformable so that the surfaces may be arranged on opposing sides of an implantable device.

It is further contemplated that fixation means cooperating on two positions of the coil arrangement opposing the intersection point are provided by means of which the orientation of the surfaces with respect to each other can be established and maintained.

The coil arrangement may be further developed in a particularly advantageous manner so that the intersection point of the coil arrangement is fixable by a coupling arrangement.

It is further particularly advantageous that the position of the intersection point and thus the dimensions of the surfaces are variable.

The invention therefore takes new findings in the field of biomechanical phenomena of the support plate screw osteosynthesis and their causal linkage to chronic infections into consideration. For example, it serves the stabilisation of multiple juxta-articular fractions of long tubular bones for which the electro-nail does not offer sufficient stability. The geometry of the screws, the secondary coils and the electrodes is fundamentally changed as compared to the devices according to the state of the art to be suitable to generate a therapeutically effective distribution of the electric fields and currents within large fragmented zones of a bone in connection with the support plate. The same applies to the dimensions and the distribution of the stimulating electric fields in the area of the socket of a hip joint replacement in the pelvic bone. The bipolar induction screws according to the invention have a length of, for example, 30 to 50 mm, preferably of 40 mm, and a cross section of, for example, 4 to 6 mm. The insulating distance of the short bipolar screws is, in contrast to the long bipolar screws (see, for example, the DE 199 28 449 C1), located between the head and the shaft of the screw. The winding around the Fe-core of the secondary coil is arranged so that the winding direction of the secondary inductivity of respectively two screws is adjusted so as to be opposing, i.e. complementary. During the screw fixation of a support plate on the bone the heads of the bipolar screws are electrically connected to each other whereby the induction coils with respectively opposing or complementary windings are connected in series. In an applicable electromagnetic field having a field intensity of, for example, 1 to 5 mT and a sinusoidal excitation frequency of 1 to 20 Hz the induced electric voltage between the shafts of two complementary screws is doubled by this arrangement. Between the shaft and the support plate contacting the screw head respectively only the simple electric voltage induced in a bipolar screw is generated.

The advantages achievable in osteosynthesis and joint endoprosthetics by a screw fixation of the metal support plates or the socket of a hip joint replacement using at least two or more of the bipolar screws according to the invention are, in particular:

The induction of identical voltages of 500 mV to 700 mV in the bone which have proven optimum in case of a solitary application of the bipolar screws having a length of 75 mm to 110 mm is achieved by the application of at least two of the 30 mm to 50 mm long, i.e. shorter bipolar screws having a complementary secondary inductivity according to the invention when fixing a support plate on the bone.

The alternating arrangement of a plurality of complementary bipolar screws enables the expansion of the induced electric field across the entire length of a support plate for stabilising and treating large defects.

The distribution of the electric field is effected over the entire cross section of the bone.

An induction of an electric voltage of approximately 250 mV to 350 mV occurs between the shaft of the individual bipolar screw and the bone support plate. In this way pressure necroses of the bone area under the support plate can be avoided.

When anchoring the socket of a hip joint replacement particularly the preservation of the vitality and stability of the pelvic bone by repeating the induction of the magnetic field of the bipolar screw fixation of the socket in optional time intervals is possible.

Independent of the actual application a drastic reduction of the risk of an infection in case of all short-term and long-term implants in osteosynthesis and joint endoprosthetics is obtained.

With the coil arrangement according to the invention it is, in addition, accomplished that the magnetic field of the two opposing loops of the coil arrangement is unidirectional due to the spatial reversal of the current direction in one of the two loops like in case of the arrangement of two separate coils according to Helmholtz. Such a coil which is, above that, elastically deformable enables the induction of implanted secondary coils largely independent of their orientation with respect to the long bone axis. A simple handling during the adjustment of the geometric shape of the coil arrangement to the position of the respective bone or soft tissue lesion is enabled. For example, the loop surfaces can be adjusted to the areas to be treated such as the foot, knee, lower leg, thigh, pelvis, backbone, hand, lower arm, upper arm, jaw or scull area by varying the loop sizes also with respect to the intensity of the magnetic field. Another feature of the coil arrangement according to the invention is an increase of the flux density in the vicinity of the intersection point so that a relatively strong magnetic field concentration to a small body section is enabled. In this manner strongly localised illnesses, such as abcesses or infections, can be effectively treated.

BRIEF DESCRIPTION OF THE DRAWINGS

The invention will now be explained by way of example quoting particularly preferred embodiments with reference to the accompanying drawings in which.

DETAILED DESCRIPTION OF THE INVENTION

In the following description of the drawings identical numerals designate identical or comparable components.

Figure 1:
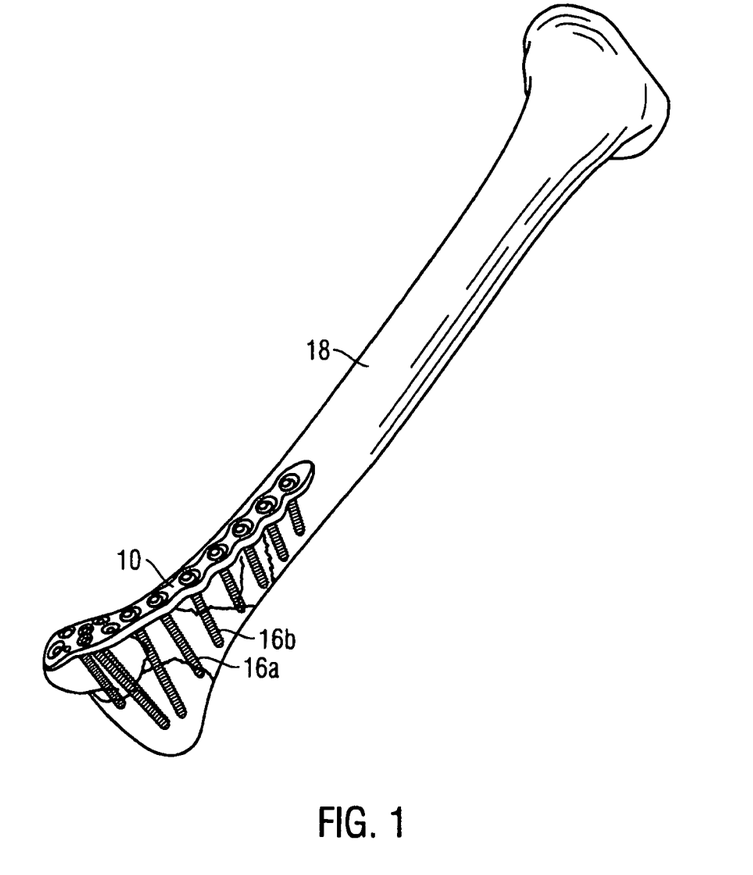
FIG. 1 is a perspective representation of a fractured bone with a bone support plate fixed by bone screws.

FIG. 1 shows a perspective representation of a fractured bone together with a bone support plate fixed by bone screws. The bone 18 is stabilised by a bone support plate 10 in the region of the fractures. The bone support plate 10 is fixed to the bone 18 with fixation screws, at least some of said fixation screws, for example the pair of screws 16a, 16b, being shaft-shaped contact means comprising coil arrangements disposed therein and wound in opposite directions, such a pair of screws also being referred to as complementary bipolar pair of screws. On principle all the screws used may be included in the concept of the complementary bipolar pairs of screws. It is also feasible that this is realised only for some or only for two of said screws. It is also possible to integrate other means than screws into the concept of the complementary contact means.

Figure 2:
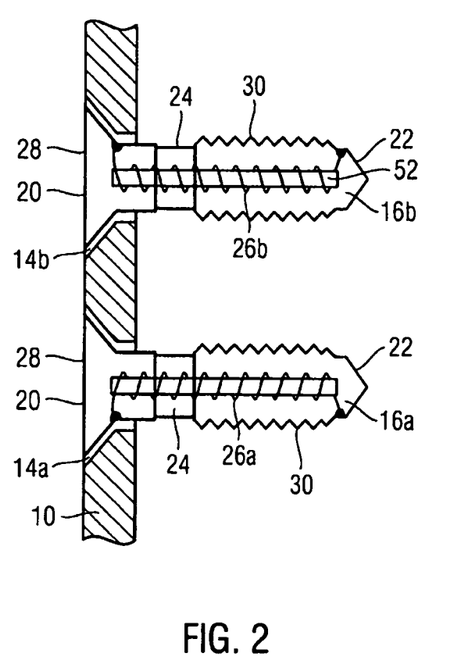
FIG. 2 is a cross sectional view of an implantable device according to the invention.

FIG. 2 shows a cross sectional view of an implantable device according to the invention. A base body 10, for example a bone support plate, is recognisable. Said base body 10 has two through holes 14a, 14b through which a respective bone screw 16a, 16b is passed. The head 28 of a respective bone screw 16a, 16b contacts the bone support plate 10 while the screw shaft 30 of the bone screws 16a, 16b is disposed in the bone and insulated with respect to the screw head 28 and therefore also with respect to the bone support plate 10 via an electrically insulating surface portion 24. In this way two surface portions 20, 22 exist which are insulated with respect to each other and, with the integration of the bone support plate 10, form counter electrodes for generating an electric field. Inside of each bone screw 16a, 16b a coil arrangement 26a, 26b is provided which is preferably wound onto a ferrite core. The poles of the coil arrangement 26a, 26b contact the sections of the bone screws 16a, 16b which are insulated with respect to each other so that in case of the presence of a magnetic field permeating the coil windings the portions of the bone screws 16a, 16b which are insulated with respect to each other are brought to different potentials. Since the screw heads 28 are both in contact with the bone support plate 10 they are on the same electric potential. Since, furthermore, the coil arrangements 26a, 26b are wound in opposite directions the potentials of the screw shafts 30 are reverse with respect to the potential of the screw heads. If voltages of identical amounts are induced in both bone screws 16a, 16b the difference between the potentials of the screw shafts 30 is twice the individual voltages induced in the respective screws 16a, 16b.

Figure 3:
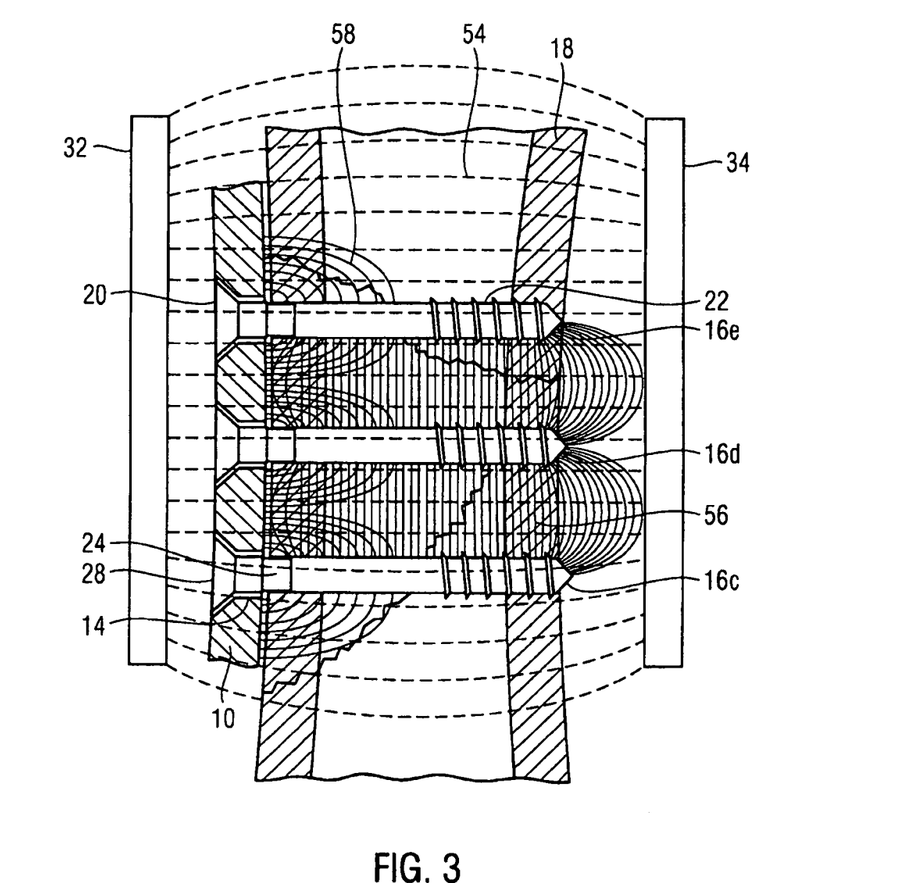
FIG. 3 is a cross sectional view of an implantable device according to the invention, namely of a bone support plate in the implanted state with an externally applied magnetic field.

FIG. 3 shows a cross sectional view of an implantable device according to the invention, namely of a bone support plate in the implanted state with an externally applied magnetic field. A bone support plate 10 is fixed to the bone 18 by means of three bone screws 16c, 16d, 16e. The bone screws 16c, 16d, 16e are structured identically or similarly, therefore the following description is exemplarily given with reference to one of the bone screws 16c. The bone screw 16c passes through a through hole 14 of the bone support plate 10. Adjacent bone screws contain coil arrangements respectively wound in opposite directions and are, aside from that, designed comparably to the bone screws described in connection with FIG. 2. Outside of the arrangement two magnetic coils 32, 34 are disposed which a wound like a pair of Helmholtz coils so that the magnetic field lines 54 represented by the broken lines are substantially parallel to the longitudinal extension of the bone screws 16c. The alternating electromagnetic field generated by the coils 32, 34 generates an electric voltage in each of the bone screws 16c, 16d, 16e, the then existing electric potentials being defined by the bone support plate 10 due to the common contact of the screw heads 28. The electric fields 56, 58 promoting the healing process and indicated by solid lines are formed between the screw shafts 30 of the respective bone screws 16c, 16d, 16e as well as between the shafts 30 of each bone screw 16c, 16d, 16e and the bone support plate 10 fixed by them. The electric field lines 56 between the screw shafts 30 of the individual screws 16c, 16d, 16e have smaller distances than the electric field lines between the screw shafts 30 and the bone support plate 10. This indicates that in case of typical distances of the components as well as a typical component design the electric fields generated by the difference between the screw potentials are larger than the electric fields generated by the smaller potential difference between the screw shafts 30 and the bone support plate 10. Actually the electric field generated by the different potentials involved has a uniform shape so that, for example, a distortion of the electric field generated by the screw shafts 30 is caused by the potential of the bone support plate 10; the field lines 56, 58 shown as intersecting in this section only represent the presence of a complex field distribution there. Further it has to be mentioned that the contribution of the potential difference between the screw shafts 30 and the bone support plate 10 to the electric field decreases with an increasing distance to the bone support plate 10 even though this is not reflected in the illustration of the field line density for reasons of simplicity.

Figure 4:
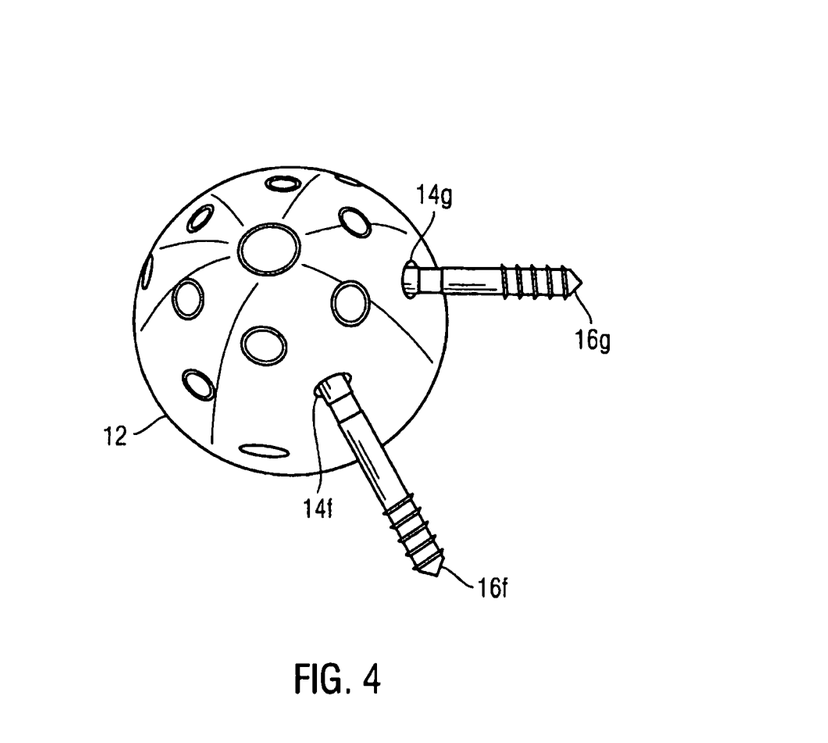
FIG. 4 is a perspective representation of an implantable device according to the invention, namely a socket of a hip joint prosthesis.

FIG. 4 shows a perspective representation of an implantable device according to the invention, namely a socket of a hip joint prosthesis. The socket 12 of the hip joint replacement includes a plurality of through holes, bone screws 16f, 16g the design of which is essentially comparable to the bone screws according to FIG. 2 being passed through the through holes 14f, 14g. Consequently the advantages of the present invention described with reference to FIGS. 1 and 3 and in connection with osteosynthesis can also be realised in connection with endoprostheses.

Figure 5:
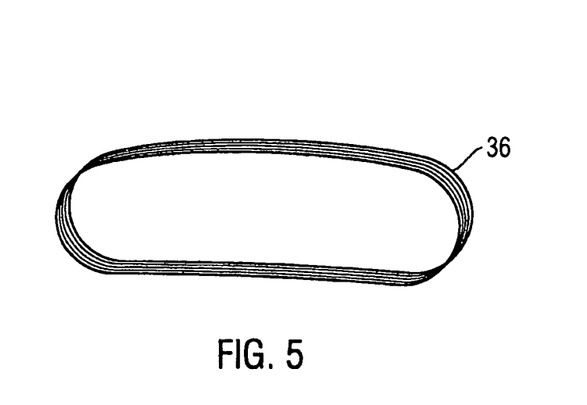
FIG. 5 is an elastic coil arrangement.
Figure 6:
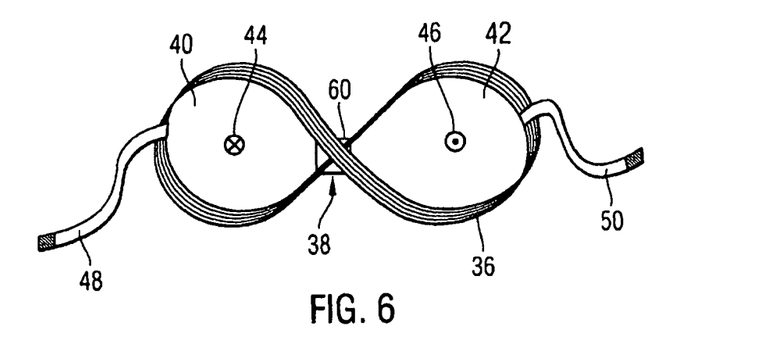
FIG. 6 shows an elastic coil arrangement according to the invention in a state outside of its application.
Figure 7:
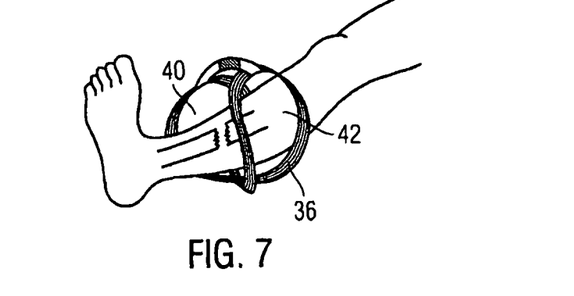
FIG. 7 is a perspective representation of a coil arrangement according to the invention during its application as a primary coil arrangement.
Figure 8:
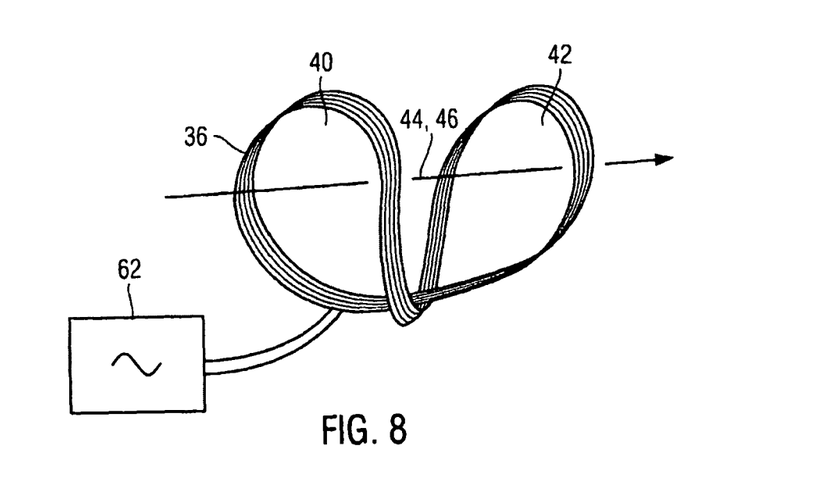
FIG. 8 is a schematic representation for explaining the spatial orientation of a magnetic field generated by a coil arrangement according to the invention.

FIG. 5 shows an elastic coil arrangement. FIG. 6 shows an elastic coil arrangement according to the invention in a state outside of its application. FIG. 7 shows a perspective representation of a coil arrangement according to the invention during its application as a primary coil arrangement. FIG. 8 shows a schematic representation for explaining the spatial orientation of a magnetic field generated by a coil arrangement according to the invention. If the elasticity of the coil arrangement 36 is used to cause it to assume an eight-shaped form two surfaces 40, 42 as well as an intersection point 38 are defined. The intersection point 38 is fixed by a coupling arrangement 60 and can preferably be shifted so that the ratio between the surfaces 40, 42 is variable. For example, an elastic strap including a Velcro type fastener or a belt buckle may serve as the coupling arrangement 60. It is also feasible to equip the surfaces of the coil arrangement so that they form the components of a Velcro type fastener and can, in this manner, directly adhere to each other in different positions. To facilitate the adjustment indications or scales may be provided in the variation range which may be used for orientation by the applicant if a certain fixation of the intersection point 38 is to be effected. If an alternating current flows through such a coil arrangement 36 the induced magnetic fields have opposite directions as indicated by the vector symbols 44, 46. Due to the elasticity of the coil arrangement 36 it can, however, also be caused to assume another form. This is shown in connection with FIG. 7 in which also a leg with a fractured bone is shown. Now the surfaces 40, 42 are positioned opposite to each other, and the magnetic fields generated in the respective segments of the coil have the same direction. This is illustrated once again in FIG. 8 in which an alternating current generator 62 coupled to the coil arrangement is also shown, namely by the uniform magnetic field vector 44, 46 passing through both surfaces 40, 42.

It will be appreciated from the above that the invention may be further characterized in accordance with the following numbered paragraphs:

1. An implantable device to be fixed to a bone and comprising
   an electrically conductive base body (10, 12) provided with at least two through holes (14) and
   at least one pair of shaft-shaped contact means (16), wherein each contact means (16) passes through a through hole (14) of the base body (10, 12) and penetrates a section of the bone (18) in an implanted state,
   wherein the surface of each contact means (16) comprises a first and a second electrically conductive surface section (20, 22) as well as an electrically insulating surface section (24) separating the electrically conductive surface sections (20, 22) from each other,
   wherein the first electrically conductive surface section (20) of each contact means (16) electrically contacts the base body (10, 12) in an implanted state while the second electrically conductive surface section (22) of each contact means (16) is electrically insulated with respect to the base body (10, 12) by means of the electrically insulating surface section (24) in an implanted state,
   wherein each contact means (16) contains a coil arrangement (26) in its interior by means of which the electrically conductive surface sections (20, 22) of each contact means are electrically coupled, and
   wherein the coil arrangements (26) of the contact means (16) of a pair are wound in opposite directions.

2. The implantable device according to paragraph 1, characterised in that at least one contact means (16) of a pair is a fixation screw contacting the base body (10) with a screw head (28) and is screwed into the bone (18) with a screw shaft (30) in an implanted state.

3. The implantable device according to paragraphs 1 or 2, characterised in that both contact means (16) of a pair are fixation screws.

4. The implantable device according to paragraphs 2 or 3, characterised in that the electrically insulating surface section of the fixation screw (16) electrically insulates the screw head (28) with respect to the main part of the screw shaft (30).

5. The implantable device according to one of the preceding paragraphs, characterised in that a plurality of pairs of shaft-shaped contact means (16) are provided, wherein respectively adjacent contact means (16) have coil arrangements (26) wound in opposite directions.

6. The implantable device according to one of the preceding paragraphs, characterised in that the base body is an osteosynthesis means (10).

7. The implantable device according to paragraph 6, characterised in that the osteosynthesis means is an implantable bone support plate (10).

8. The implantable device according to one of the paragraphs 1 to 5, characterised in that the base body is an endoprosthesis (12).

9. The implantable device according to paragraph 8, characterised in that the base body is the socket (12) of a joint replacement.

10. A system for generating localised electromagnetic fields in the area of an implant comprising
    an implantable device to be fixed to a bone, particularly according to one of the preceding claims, comprising
      an electrically conductive base body (10, 12) provided with at least two through holes (14) and
      at least one pair of shaft shaped contact means (16), wherein each contact means (16) passes through a through hole (14) of the base body (10, 12) and penetrates a section of the bone (18) in an implanted state,
      wherein the surface of each contact means (16) comprises a first and a second electrically conductive surface section (20, 22) as well as an electrically insulating surface section (24) separating the electrically conductive surface sections (20, 22) from each other,
      wherein the first electrically conductive surface section (20) of each contact means (16) electrically contacts the base body (10, 12) in an implanted state while the second electrically conductive surface section (22) of each contact means (16) is electrically insulated with respect to the base body (10, 12) by means of the electrically insulating surface section (24) in an implanted state,
      wherein each contact means (16) comprises a secondary coil arrangement (26) in its interior by means of which the electrically conductive surface sections (20, 22) of each contact means are electrically coupled, and
      wherein the secondary coil arrangements (26) of the contact means (16) of a pair are wound in opposite directions, and comprising a primary coil arrangement (32, 34, 36) generating an electromagnetic field in the area of the contact means (16) as well as an oscillation generator (62) for generating an alternating current in the primary coil arrangement (32, 34, 36).

11. The system according to paragraph 10, characterised in that the primary coil arrangement (36) includes a coil winding having a point of intersection (38) and defining two surfaces (40, 42) by means of an eight-shaped form, said surfaces (40, 42) being oriented with respect to each other at least during the application of the primary coil arrangement (36) so that the magnetic fields (44, 46) generated by a current flow in the primary coil arrangement (36) and passing through the surfaces are substantially unidirectional.

12. The system according to paragraph 11, characterised in that the primary coil arrangement (36) is elastically deformable so that the surfaces can be arranged on opposing sides of the implantable device.

13. The system according to paragraph 11 or 12, characterised in that fixation means (48, 50) cooperating at two positions of the primary coil arrangement opposed to the intersection point (38) are provided by means of which fixation means the orientation of the surfaces (40, 42) with respect to each other can be established and maintained.

14. The system according to paragraph 12 or 13, characterised in that the intersection point (38) of the primary coil arrangement is fixable by means of a coupling arrangement (60).

15. The system according to one of paragraphs 12 to 14, characterised in that the position of the intersection point (38) and therefore the dimensions of the surfaces (40, 42) are variable.

16. A coil arrangement, particularly for the utilisation in a system for generating localised electromagnetic fields in the area of an implant according to one of paragraphs 11 to 15, comprising a coil winding including an intersection point (38) and defining two surfaces (40, 42) by means of an eight-shaped form, the surfaces (40, 42) being oriented with respect to each other so that the magnetic fields (44, 46) generated by a current flow in the coil arrangement (36) and passing through the surfaces are substantially unidirectional.

17. The coil arrangement according to paragraph 16, characterised in that the coil arrangement (36) is elastically deformable so that the surfaces (40, 42) can be arranged on opposing sides of an implantable device.

18. The coil arrangement according to paragraph 16 or 17, characterised in that fixation means (48, 50) cooperating on two positions of the coil arrangement opposing the intersection point (38) are provided by means of which the orientation of the surfaces (40, 42) with respect to each other can be established and maintained.

19. The coil arrangement according to one of the paragraphs 16 to 18, characterised in that the intersection point (38) of the coil arrangement is fixable by means of a coupling arrangement (60).

20. The coil arrangement according to one of the paragraphs 16 to 19, characterised in that the position of the intersection point (38) and thus the dimensions of the surfaces (40, 42) are variable.

The features of the invention disclosed in the above description, in the drawings as well as in the claims may be important for the realisation of the invention individually as well as in any combination.

LIST OF NUMERALS

10 basic body/bone support plate
12 basic body/endoprosthesis/socket
14 through hole
16 contact means/fixation means
18 bone
20 surface portion
22 surface portion
24 surface portion/insulation
26 coil arrangement/secondary coil arrangement
28 screw head
30 screw shaft
32 primary coil arrangement/magnetic coil
34 primary coil arrangement/magnetic coil
36 primary coil arrangement
38 intersection point
40 surface
42 surface
44 magnetic field/magnetic field vector/vector symbol
46 magnetic field/magnetic field vector/vector symbol
48 fixation means
50 fixation means
52 ferrite core
54 magnetic field
56 electric field
58 electric field
60 coupling arrangement
62 alternating current generator

What is claimed is:

1. An implantable device to be fixed to bone and comprising:
   an electrically conductive base body provided with at least two through holes and
   at least one pair of shaft-shaped contact means, wherein each of the contact means passes through a through holes of the base body and is adapted to penetrate a section of the bone in an implanted state,
   wherein the surface of each of the contact means comprises:
      a first electrically conductive surface section,
      a second electrically conductive surface section, and
      an electrically insulating surface section separating the electrically conductive surface sections from each other,
   wherein the first electrically conductive surface section of each of the contact means electrically contacts the base body in an implanted state while the second electrically conductive surface section of each of the contact means is electrically insulated with respect to the base body by means of the electrically insulating surface section in an implanted state,
   wherein an interior of each of the contact means contains a coil arrangement, each of the coil arrangements having:
      two electrical poles,
      a first electrical pole being electrically coupled with the first electrically conductive surface section, and
      a second electrical pole being electrically coupled with the second electrically conductive surface section of each of the contact means, and
   wherein the coil arrangements of the contact means of a pair are wound in opposite directions so that when an alternating magnetic field is permeating the coil arrangements for powering, the second electrically conductive surface sections of the pair have an electrical potential difference that is the sum of the electrical potential differences between the electrically conductive surface section of each of the pair of the contact means.

2. The implantable device according to claim 1, wherein at least one of the contact means of a pair is a fixation screw contacting the base body with a screw head and is adapted to be screwed into the bone with a screw shaft in an implanted state.

3. The implantable device according to claim 2, wherein both of the contact means of a pair are fixation screws.

4. The implantable device according to claim 3, wherein the electrically insulating surface section of the fixation screw electrically insulates a screw head with respect to a main part of a screw shaft of the fixation screw.

5. The implantable device according to claim 4, wherein the base body is an endoprosthesis.

6. The implantable device according to claim 5, wherein the base body is a socket of a joint replacement.

7. The implantable device according to claim 1, wherein a plurality of pairs of shaft-shaped contact means are provided, wherein respectively adjacent contact means have coil arrangements wound in opposite directions.

8. The implantable device according to claim 1, wherein the base body is an osteosynthesis means.

9. The implantable device according to claim 8, wherein the osteosynthesis means is an implantable bone support plate.

10. A system for generating localized electromagnetic field in the area of an implant comprising
an implantable device to be fixed to a bone, comprising
an electrically conductive base body provided with at least two through holes and
at least one pair of shaft-shaped contact means, wherein each of the contact means passes through a through holes of the base body and is adapted to penetrate a section of the bone in an implanted state,
wherein the surface of each of the contact means comprises:
a first electrically conductive surface section,
a second electrically conductive surface section, and
an electrically insulating surface section separating the electrically conductive surface sections from each other,
wherein the first electrically conductive surface section of each of the contact means electrically contacts the base body in an implanted state while the second electrically conductive surface section of each of the contact means is electrically insulated with respect to the base body by means of the electrically insulating surface section in an implanted state,
wherein an interior of each of the contact means comprises a secondary coil arrangement, each coil arrangement having:
two electrical poles,
a first electrical pole being electrically coupled with the first electrically conductive surface section, and
a second electrical pole being electrically coupled with the second electrically conductive surface section of each of the contact means, and
wherein the secondary coil arrangements of the contact means of a pair are wound in opposite direction so that when an alternating magnetic field is permeating the coil arrangements for powering, the second electrically conductive surface section of the pair have an electrical potential difference that is the sum of the electrical potential differences between the electrically conductive surface sections of the contact means of the pair, and comprising
a primary coil arrangement generating an electromagnetic field in the area of the contact means, and
an oscillation generator for generating an alternating current in the primary coil arrangement.

11. The system according to claim 10, wherein the primary coil arrangement includes a coil winding having a point of intersection and defining two surfaces by means of an eight-shaped form, said surfaces being oriented with respect to each other at least during the application of the primary coil arrangement so that the magnetic fields generated by a current flow in the primary coil arrangement and passing through the surfaces are substantially unidirectional.

12. The system according to claim 11, wherein the primary coil arrangement is elastically deformable so that the surfaces can be arranged on opposing sides of the implantable device.

13. The system according to claim 12, wherein fixation means cooperating at two positions of the primary coil arrangement opposed to the intersection point are provided by means of which fixation means the orientation of the surfaces with respect to each other can be established and maintained.

14. The system according to claim 13, wherein the intersection point of the primary coil arrangement is fixable by means of a coupling arrangement.

15. The system according to claim 14, wherein the position of the intersection point and therefore the dimensions of the surfaces are variable.

* * * * *

UNITED STATES PATENT AND TRADEMARK OFFICE
CERTIFICATE OF CORRECTION

PATENT NO. : 8,425,395 B2  
APPLICATION NO. : 12/126455  
DATED : April 23, 2013  
INVENTOR(S) : Kraus et al.

Page 1 of 1

It is certified that error appears in the above-identified patent and that said Letters Patent is hereby corrected as shown below:

Title Page, OTHER PUBLICATIONS, delete

"Yunokichi K et al.: "Developing a More Focal Magnetic Stimulator. Opart II: Fabricating Coils and Measuring Induced Current Distributions" Journal of Clinical Neurophysiology, Rave~ Press, New York, NY, US, Bd. 8, Nr. 1, 1. Jan 1991."

Signed and Sealed this  
Twenty-second Day of October, 2013

Teresa Stanek Rea  
*Deputy Director of the United States Patent and Trademark Office*